United States Patent [19]
Panchula

[11] Patent Number: 5,100,406
[45] Date of Patent: Mar. 31, 1992

[54] SILICONE BREAST PUMP INSERT

[75] Inventor: Martin Panchula, Creve Coeur, Mo.

[73] Assignee: Graham-Field, Inc., Hauppauge, N.Y.

[21] Appl. No.: 607,573

[22] Filed: Nov. 1, 1990

[51] Int. Cl.⁵ .................................. A61M 1/06
[52] U.S. Cl. ........................... 606/74; 604/75
[58] Field of Search ............ 604/74, 75, 76, 73, 604/231, 346

[56] References Cited

U.S. PATENT DOCUMENTS

| | | | |
|---|---|---|---|
| 1,509,226 | 9/1924 | Brown | 604/74 |
| 1,670,610 | 5/1928 | Colby | 604/74 |
| 2,542,505 | 2/1951 | Gascoigne | 604/74 |
| 4,573,969 | 3/1986 | Schlensog | 604/74 |
| 4,772,262 | 9/1988 | Grant | 604/74 |
| 4,794,915 | 1/1989 | Larsson | 604/74 |
| 4,799,922 | 1/1989 | Beer | 604/74 |
| 4,813,932 | 3/1989 | Hobbs | 604/74 |

Primary Examiner—Robert A. Hafer
Assistant Examiner—Michael Brown
Attorney, Agent, or Firm—Bauer & Schaffer

[57] ABSTRACT

A liner for a breast pump which results in increased milk pumped from the female breast having a bell-shaped, flexible body which flares outwardly at one end to a size sufficient to fit over the female breast and narrows at the opposite end to an opening of a size sufficient to permit the flow of milk and which is provided with a circular extension to be connected to the pumping head. The body is provided on its outer surface with recesses providing a membranous wall portion thinner than the body.

8 Claims, 1 Drawing Sheet

SILICONE BREAST PUMP INSERT

This invention relates to a liner for the cup of a breast pump and more particularly to a removable elastomeric insert for the pump head of a milk collection system to increase comfort to the wearer and to increase the amount of milk drawn from the breast.

BACKGROUND OF THE INVENTION

A wide variety of breast pump systems are known and are commercially available. For example, the Egnell Lact-E electric pump may be used with the collection kit by Medela or the collection kit by G. E. While such breast systems are generally acceptable and accomplish their intended purpose, they still exhibit certain disadvantages. For example, they are to some extent inefficient in that they do not pump as large a quantity of milk from a breast during a reasonable pumping period and thus must be used repeatedly in order to collect the required amount of milk. Of equal or even more importance is the fact that the cup is difficult to maintain in place under pump action and is uncomfortable to the user, particularly when the breast is full and sensitive.

There exists, therefore, a need for breast pump arrangements which do not exhibit the above-mentioned disadvantages. The objects of the present invention are to overcome these disadvantages.

BRIEF STATEMENT OF THE INVENTION

In accordance with the invention, there is provided a removable elastomeric liner for the cup or pump head of a breast collector, comprising a bell-shaped flexible body which flares outwardly to a circumferential perimetric opening at one end and which is of a size sufficient to fit over a substantial portion of the breast, and a smaller circumferential perimetric opening located at the opposite end or apex of the body which is provided with a circular extension adapted to be connected to the socket of the pumping head or drainage tube of the collection system.

A plurality of arcuately arranged oval recesses are formed in the exterior surface of the body, midway between the perimetric openings to provide in the elastomeric body a thin membrane at the areola area of the breast. As a result, the sucking action produced during the pump stroke is longer in duration than would be otherwise possible, thus increasing milk production as well as being softer and more comfortable to the wearer, consequently significantly reducing medical complications.

Full details of the present invention are set forth in the following disclosure and in the accompanying drawings.

THE DRAWINGS

In order to describe this invention more fully, reference is directed to the accompanying drawings in which.

DESCRIPTION OF THE PREFERRED EMBODIMENTS

Figure 1:
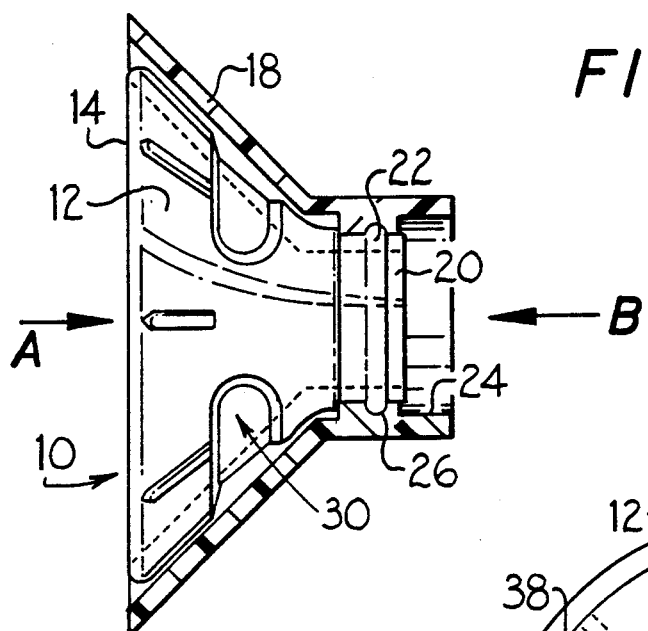
FIG. 1 is a side view of the elastomeric liner according to the invention shown in combination with the pump head or cup of the collection system.

Referring now to the drawings, the liner according to the invention comprises a bell-shaped elastomerice body 10 comprising a relatively thick but flexible conical wall 12 which flares outwardly to an enlarged circumferential opening 14 at one end and a smaller opening 16 at its opposite end. The opening 14 is sufficiently large to permit the body 10 to fit over a substantial portion of the female breast. More preferably the body 10, including the perimetric edge forming the opening 14, conforms to the shape of the pump head or cup 14 illustrated by the numeral 18. The smaller opening 16, serving as the drainage outlet, is formed with a cylindrical extension 20 having an outer surface of reduced diameter on which is provided a ring-like bead 22. The cylindrical extension 20 is adapted to fit into the central socket 24 of a pump head 18 with the bead 22 firmly locked into a receiving groove 26 formed therein or to the drainage tube passing out from the pump head.

The body 10 is preferably made of soft flexible silicone plastic which is readily moldable or castable at reasonable costs as well as being inert and thus harmless to the human body. It may, however, be made of other suitable, soft, elastomeric materials which are inert to the human body. Such materials include latex, polyvinyl chloride, nylon, polyester, and acrylic plastics and the like. The body is preferably molded or cast by any of the conventional plastic forming processes.

Figure 2:
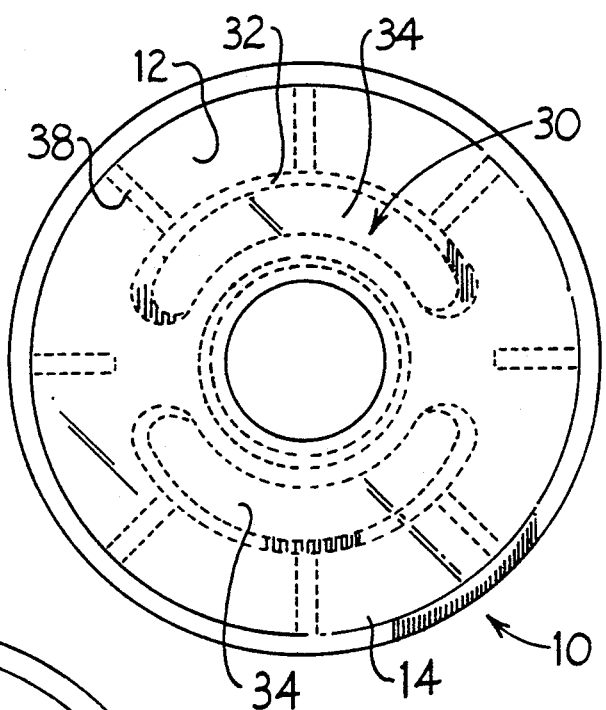
FIG. 2 is a plan view of the liner, taken in the direction of Arrow A in FIG. 1, omitting the collection system.
Figure 3:
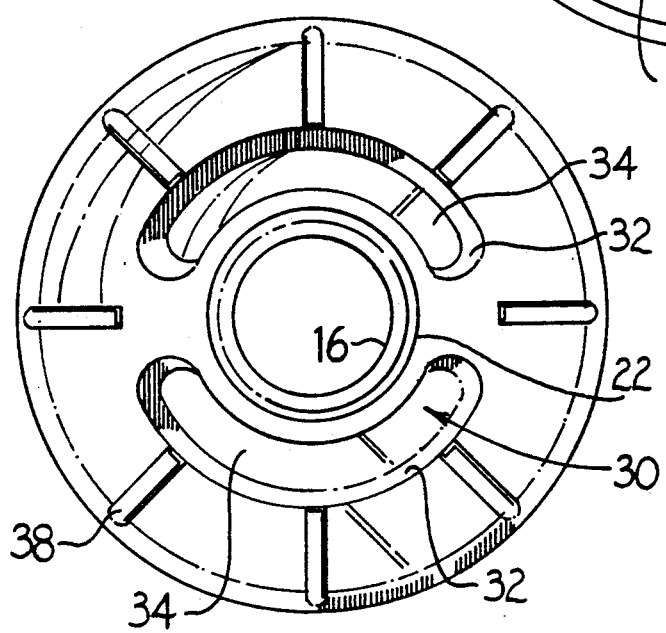
FIG. 3 is a plan view of the liner taken from the opposite end in the direction of Arrow B in FIG. 1, also omitting the collection system.

As may be further seen in FIGS. 1 and 2, the outer surface of the conical wall 12 of the elastomeric body is provided with a pair of recesses 30 located between ends defining openings 14 and 16 so as to be in diametric opposition to each other in the vicinity of the areola of the breast. Each recess is bounded by a bevelled edge 32 to provide a gradual slope to a wall 34 at the bottom of the recess. The bottom wall 34 is integrally and unitarily formed with the remaining portions of the body and provides a thin membrane of relatively greater flexibility and softness than the remaining wall of the body. In plan view each of the recesses 30 are of a kidney or oval shape and follow the curvature of the conical wall 12 about its central axis and follows the curvature of the areola. Each of the recesses 30 extend in overall length through an arc of between 90° and 150° and have a width of approximately 0.35 inches. The membrane forming the bottom wall 34 in each recess 30 may be about 0.03 inches thick, while the remaining wall section of the elastomeric body may have a thickness of 0.1 inch. As a result the membrane forming the bottom wall of each recess is highly flexible, and because of the relatively large space created by the recess 30, the membrane will move readily under the influence of both the suction stroke of the pump and the pressure of milk discharging from the breast.

Completing the structure of the body 10 are a plurality of axially directed ribs 38 located on the outer surface of the conical wall 12. The ribs 38 are uniformly spaced radially about the central axis of the body between the larger opening 14 and the recesses 30. In addition to providing added strength to the body, the ribs 38 provide a space between the surfaces of the conical wall 12 and the pump head 18 to allow passage of air to the recessed areas and a degree of adjustability when fitted to the breast.

A breast pump system employing the inventive liner 10 was assembled using a G.E. milk collection kit attached to an Egnell Lact-E electric pump. For comparison purposes a Medela milk collection kit, provided with a similar electric pump but without the liner of the present invention, was also assembled.

The pumping head of each assembly was placed respectively on equally full breasts, and, with both pumps set at normal, pumping was undertaken for three minutes; then the pumping heads were switched to opposite breasts for an additional three minutes. The quantity of milk pumped was measured at the end of the first and second three-minute periods. The milk Ejection Reflex (MER) or let down occurred at one minute into pumping. The results are set forth in the table below.

| LEFT BREAST | RIGHT BREAST |
|---|---|
| Medela Kit (without liner) | G.E. Kit (with liner) |
| 1st three-minute pumping | |
| 37 ml. | 40 ml. |
| G.E. Kit (with liner) | Medela Kit (without liner) |
| 2nd three-minute pumping | |
| 37 ml. | 16 ml. |
| Total milk with the G.E. Kit and inventive liner = 77 ml. | |
| Total milk with the Medela Kit (no liner) = 53 ml. | |

It is obvious that even after the initial depletion of milk from the breast, the kit having the liner of the present invention was able to pump at least as much milk in the second three-minute period as the comparison system produced in the first three-minute period. Further, the users reported greater comfort and lower fatigue when using the present invention.

Numerous additional tests were made using different collection kits, all resulting in a showing that an increased amount of milk could be pumped when the liner of the invention is employed.

It will be obvious, therefore, that the elastomeric liner of the present invention overcomes the disadvantages enumerated earlier and enables greater milk drainage and greater comfort.

Various modifications and changes have been noted, and others will be apparent to those skilled in the art. Accordingly, it is to be understood that the present disclosure is to be taken as illustrative and not limiting of the present invention.

What is claimed is:

1. A liner insertable in the pump head of a breast pump system to enhance the extraction of milk comprising an elastomeric body conforming in shape to the pump head and having at least one recess in its outer surface, said recess having a membranous bottom wall thinner than that of the remaining portions of the body.

2. The liner according to claim 1 wherein said body comprises a conical wall, one end of which flares outwardly to fit over a substantial portion of the breast and the other end of which narrows into an outlet for the flow of milk and having integrally formed therewith a cylindrical extension.

3. The liner according to claim 2 including two or more recesses, each of said recesses having an arcuate shape and being arranged in opposition to each other between the ends.

4. The liner according to claim 3 wherein said recesses have an arcuate extent of between 90° to 150°.

5. The liner according to claim 1 which is made of flexible silicone plastic or similar material.

6. The liner according to claim 1, including a plurality of uniformly spaced axially directed ribs on the exterior surface of said body.

7. In combination with a breast pump system having a pumping head, milk collection wall, and means for actuating said pumping head, a liner for insertion in said pumping head comprising a bell-shaped flexible body which flares outwardly to a circumferential perimetric opening at one end and which is of a size sufficient to fit over a female breast, a smaller circumferential perimetric opening located at the opposite end of said body which is of a size at least sufficient to permit the flow of milk therefrom and which is provided with a circular extension adapted to be connected to said pumping head of said breast pump, said liner comprising a unitary molded elastomeric body conforming in shape to the pump head and having at least one recess in its outer surface, said recess having a membranous bottom wall thinner than that of the remaining portions of the body.

8. The combination according to claim 7, wherein the recesses are located on the external surface of the body, between the circumferential perimetric openings in the general vicinity of the areola.

* * * * *